(12) United States Patent
Abrignani et al.

(10) Patent No.: US 7,807,438 B2
(45) Date of Patent: Oct. 5, 2010

(54) PREPARATION OF PURIFIED EXOSOMES COMPRISING HCV RNA

(75) Inventors: Sergio Abrignani, Siena (IT); Piero Pileri, Siena (IT)

(73) Assignee: Novartis AG, Basel (CH)

( * ) Notice: Subject to any disclaimer, the term of this patent is extended or adjusted under 35 U.S.C. 154(b) by 272 days.

(21) Appl. No.: 11/699,925

(22) Filed: Jan. 30, 2007

(65) Prior Publication Data

US 2007/0254351 A1  Nov. 1, 2007

Related U.S. Application Data

(62) Division of application No. 10/130,467, filed as application No. PCT/IB00/01801 on Nov. 20, 2000, now Pat. No. 7,198,923.

(30) Foreign Application Priority Data

Nov. 18, 1999  (GB)  ................................ 9927320.3

(51) Int. Cl.
*C12N 7/02* (2006.01)
*C12Q 1/70* (2006.01)
*C12Q 1/68* (2006.01)
*C07H 21/02* (2006.01)

(52) U.S. Cl. ................................ 435/239; 435/5; 435/6; 435/7.1; 536/23.72

(58) Field of Classification Search ........................ None
See application file for complete search history.

(56) References Cited

U.S. PATENT DOCUMENTS 5,959,092 A * 9/1999 Miyamura et al. ........ 536/23.72
7,198,923 B1 * 4/2007 Abrignani et al. .......... 435/91.1

FOREIGN PATENT DOCUMENTS

| WO | WO 91/15574 A1 | 10/1991 |
| WO | WO 96/05513 A1 | 2/1996 |
| WO | WO 97/05900 A1 | 2/1997 |
| WO | WO 97/09349 A1 | 3/1997 |
| WO | WO 99/18198 A1 | 1/1999 |
| WO | WO 99/24054 A1 | 4/1999 |
| WO | WO 99/03499 A1 | 5/1999 |

OTHER PUBLICATIONS

Nagasaka et al., "Differential flotation centrifugation study of hepatitis C virus and response to interferon therapy," Journal of Medical Virology, vol. 52 No. 2, pp. 190-194 (1997).*
Escola, et al., "Selective Enrichment of Tetraspan Proteins on the Internal Vesicles of Multivesicular Endosomes and on Exosomes Secreted by Human B-Lymphocytes," *J. Biol Chem.* 273:20121-20127 (1998).
Harding, et al., "Immunogenic Peptides Bind to Class II MHC Molecules in an Early Lysosomal Compartment," *J. Immunol.* 151:3988-3998 (1993).
Heddini, et al., "Enrichment of Immunoglobulin Binding Plasmodium Falciparum-Infected Erythrocytes Using Anti-Immunoglobulin Coated Magnetic Beads," *Am. J. Trop. Med Hyg.* 59:663-666 (1998).
Neefjes, et al., "The Biosynthetic Pathway of MHC Class II but not Class I Molecules Intersects the Endocytic Route," *Cell* 61:171-183 (1990).
Pileri, et al., "Binding of Hepatitis C Virus to CD81," *Science* 282:938-941 (1998).
Raposos, et al., "B Lymphocytes Secrete Antigen-Presenting Vesicles," *J. Exp. Med.* 183:1161-1172 (1996).
Tulp, et al., "Isolation and Characterization of the Intracellular MHC Class II Compartment," *Nature* 369:120-126 (1994).

* cited by examiner

*Primary Examiner*—Zachariah Lucas
(74) *Attorney, Agent, or Firm*—Mark Seka; Roberta Robins

(57) ABSTRACT

The invention relates to a method for isolation of hepatitis C virus. The method comprises the separation of particles termed exosomes from the blood plasma of an individual infected with hepatitis C virus (HCV) and the extraction or RNA from these exosome particles.

14 Claims, 3 Drawing Sheets

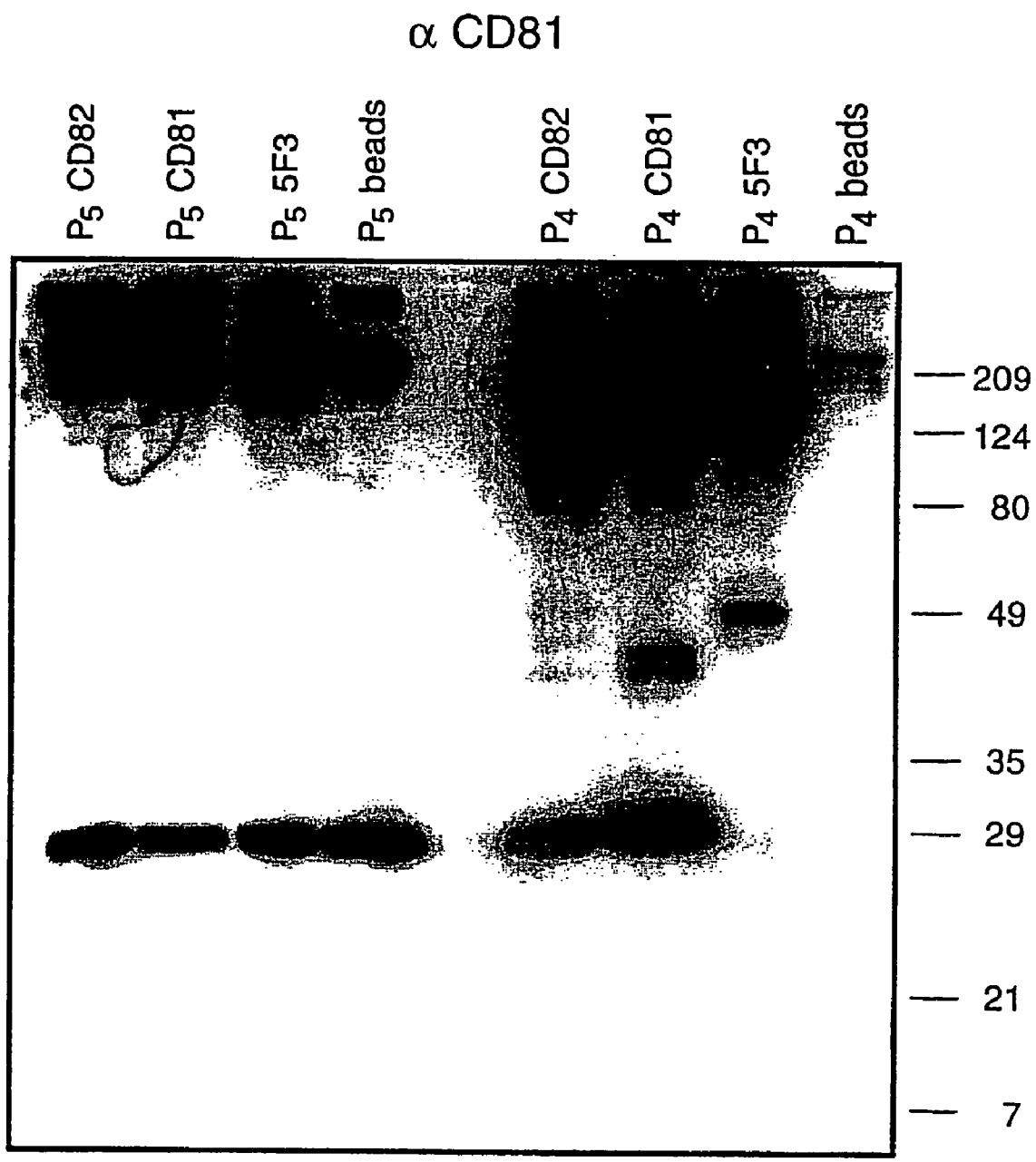

PREPARATION OF PURIFIED EXOSOMES COMPRISING HCV RNA

This application is a divisional application of U.S. patent application Ser. No. 10/130,467, filed Feb. 26, 2003, now U.S. Pat. No. 7,198,923, which is a 371 filing of PCT/IB00/01801, filed Nov. 20, 2000, which claims priority to GB 9927320.3, filed Nov. 18, 1999, from which applications priority is claimed pursuant to the provisions of 35 U.S.C. §§119/120, and which applications are hereby incorporated by reference in their entireties.

The present invention relates to a method for the isolation of hepatitis C virus. The method comprises the separation of particles termed exosomes from the blood plasma of an individual infected with hepatitis C virus (HCV) and extracting RNA from these exosome particles.

All publications, manuals, patents, and patent applications cited herein are incorporated in full by reference.

HCV (previously known as Non-A Non-B hepatitis—NANBV) is a positive sense RNA virus of about 10000 nucleotides with a single open reading frame encoding a polyprotein of about 3000 amino acids. Although the structure of the virus has been elucidated by recombinant DNA techniques (European patent application EP-A-0318216 and European patent application EP-A-0388232), the virus itself has not been isolated and the functions of the various viral proteins produced by proteolysis of the polyprotein have only been inferred by analogy with other similar viruses of similar genomic organisation (Choo et al PNAS USA (1991) 88 2451-2455).

The viral proteins are all available in recombinant form, expressed in a variety of cells and cell types, including yeast, bacteria, insect, plant and mammalian cells (Chien, D. Y. et al PNAS USA (1992) 89 10011-10015 and Spaete, R. R. et al Virology (1992) 188 819-830).

Two proteins, named E1 and E2 (corresponding to amino acids 192-383 and 384-750 of the HCV polyprotein respectively, numbered relative to the HCV-1 isolate) have been suggested to be external proteins of the viral envelope which are responsible for the binding, of virus to target cells.

HCV research is hindered very considerably by the limited host range of the virus. The only reliable animal model for HCV infection is the chimpanzee. Study of HCV life cycle has also been limited by the lack of an efficient cell culture system. Furthermore, attempts to purify HCV from biological materials such as plasma and liver have failed.

In our copending International patent application PCT/IB95/00692 (WO 96/05513), we describe a method employing flow cytometry to identify cells carrying the HCV receptor. We have shown that, by labelling cells with recombinant E2 envelope protein, it is possible to sort cells using flow cytometry, isolating those cells capable of specific binding to the E2 and therefore potentially carrying an HCV receptor.

In our copending International patent application PCT/IB96/00943 (WO 97/09349), we have identified a protein capable of binding to the E2 envelope protein of HCV.

In our copending International patent application PCT/IB98/01628 (WO99/18198), we reported the cloning of the DNA encoding a receptor for HCV. This DNA corresponds to the gene that encodes a known cellular protein, CD81.

However, despite the identification of this receptor for HCV, there remains a great need for a method that would allow the simple preparation of the RNA genome of HCV. This would considerably facilitate the progress of research into the biology of this virus and would accelerate the design of therapeutic and diagnostic reagents that are effective in the treatment and prevention of disease associated with Hepatitis C infection.

SUMMARY OF THE INVENTION

According to the present invention, there is provided a method for the preparation of HCV comprising separating exosome particles from the supernatant of a cellular culture infected with HCV and extracting RNA from the exosome particles. Preferably, the exosome particles are separated from the plasma of an individual infected with HCV.

It has been discovered that in individuals infected with HCV, the virus binds to exosome particles in the plasma and is concentrated in these particles. The purification of these particles thus allows the simple preparation of significant quantities of HCV RNA without the need for complicated or expensive purification procedures.

Exosomes are subcellular organelles that result from the fusion of endocytic compartments, termed MIICs (MHC class II-enriched compartments) with the plasma membrane. These compartments have been shown to exist in antigen-presenting cells (APCs), and form a site for the localisation of the majority of intracellular MHC class II molecules (Neefjes et al., 1990). MIICs are endocytic vacuoles with internal membrane vesicles and sheets, and are thought to represent the subcellular site at which MHC class II molecules bind peptides (Harding et al., 1993). MIICs contain internal vesicles (exosomes) that probably originate from the inward vesiculation of its limiting membrane. When MIICs fuse with the plasma membrane, inserting MHC class II molecules into this structure, the exosomes are released into the extracellular space.

Exosome particles have now been found in cell culture medium from a variety of APCs, such as dendritic cells, tonsil B cells, monocytes and macrophages (Raposo et al., 1996). These exosomes have been characterised by Geuze and coworkers (Escola, 1998) and found to be selectively enriched in some surface molecules, including certain tetraspanin membrane proteins.

By the term "supernatant of a cellular culture" is meant the supernatant of any fluid in which cells infected with HCV are grown. Suitable fluids include bodily fluids such as blood, and growth medium in which cells are cultured in vitro.

In one embodiment, exosomes may be prepared from the cell culture supernatant of cell lines derived from patients infected with HCV. Such cell lines may be expanded from individual cells isolated from patients infected with HCV and propagated in vitro.

In an alternative embodiment, exosomes may be isolated from the plasma fraction of an individual infected with HCV. Techniques for the separation of plasma from blood will be clear to the skilled reader.

The individual from which blood plasma is taken for preparation of exosomes may be any animal susceptible to infection by HCV. Suitable animals include primates, preferably higher primates such as chimpanzees and humans. Most preferably, exosomes are prepared from human patients.

Exosome particles may be prepared from cell culture supernatant using any suitable technique, as will be clear to those of skill in the art. Examples include preparation by differential centrifugation, and using techniques of immunochemistry discussed below. Preferably, exosomes are prepared by differential centrifugation, according to the technique of Raposo et al. (1996).

According to one embodiment of the invention, there is provided a method for the preparation of HCV RNA comprising the sequential steps of centrifuging plasma obtained from an individual infected with HCV to give a pellet that is enriched in exosomes, and isolating said RNA from said exosomes.

Preferably, the centrifugation is performed sequentially in iterative steps. These steps involve centrifugation firstly at approximately 200×g, then at approximately 500×g, at approximately 2000×g, at approximately 10000×g, and at approximately 70000×g.

Samples of pellets obtained at each centrifugation step can be analysed to assess the degree of exosome content and thus to gauge the purity of the exosome preparations. The preparation process can in this way be optimised. One technique that is suitable for analysing exosome content is by SDS-PAGE and Western blotting, using antibodies directed against proteins that are specific markers for exosome particles. Antibodies directed against CD81 and/or CD82 are particularly suitable in this respect. Binding of these primary antibodies to exosomes can be assessed using, for example, labelled secondary antibodies that bind to the primary antibodies. For example, anti-CD81 monoclonal antibody can be used as the primary antibody, whilst a labelled anti-mouse IgG can be used as the secondary antibody.

In a preferred embodiment of this aspect of the invention, exosomes may be prepared as followed. Cell cultures are first centrifuged for 10 minute at 200×g and recovered cells represent pellet P1. Removed supernatant is centrifuged twice for 10 minute at 500×g; the two pellets are pooled and represent pellet P2. Supernatants are sequentially centrifuged at 2000×g twice for 15 minute (pooled pellets are referred to as P3), once at 10000×g for 30 minute (recovered pellet represents pellet P4) and once at 70000×g for 60 minute (yielding pellet P5). Samples of each pellet are then analysed in SDS-PAGE and Western blotting by using anti-CD81 monoclonal antibody followed by peroxidase-labelled anti-mouse IgG.

As mentioned above, techniques of immunochemistry may be used as an alternative to the techniques of differential centrifugation. These techniques may also be used in conjunction with differential centrifugation to give more pure preparations of exosomes.

For example, the cell culture supernatant may be incubated with beads coated with antibody that recognises marker molecules on the surface of exosome particles. For example, anti-CD81 and/or anti-CD82 antibodies may be used in this respect. As the skilled reader will appreciate, magnetic beads, such as those manufactured by Dynabeads, Dynal, Oslo, Norway, or polystyrene beads (for example, those made by Pierce) are particularly suitable in this embodiment of the invention. Other alternatives for the purification of exosomes include the use of sucrose density gradients or organelle elecrophoresis (Tulp et al., 1994).

"Bona fide" HCV particles consisting of envelope-associated HCV RNA may be associated with or contained in exosomes. RNA may be prepared from the exosomes by any suitable technique, as will be clear to the skilled reader. Suitable methods for RNA extraction are well known in the art (see, for example Sambrook et al., (1989) Molecular Cloning: a laboratory manual; Cold Spring Harbor Press). Commercially-available RNA extraction kits may be used for convenience, such as the viral extraction kit sold by Qiagen, which uses silica gel based spin columns that allow purification of viral nucleic acids from cell-free body fluids.

According to a still further aspect of the invention, there is provided a preparation of purified HCV particles. Preferably, the HCV particles are prepared according to any one of the methods described above. Due to technical difficulties involved in the preparation of HCV particles, no composition of purified HCV particles have yet been made. The method of the invention thus allows, for the first time, purified HCV particles to be prepared. The method of the invention therefore allows, for the first time, the biochemical and biophysical characterisation of HCV particles and proteins.

Purified HCV particles prepared according to the invention may be used in numerous applications, as the skilled reader will appreciate. Such applications include the diagnosis, prevention and treatment of individuals infected with HCV and the development and design of agents useful in therapy, prevention and diagnosis of this disease and its progression.

According to a further aspect of the invention there is provided a method of diagnosing an individual as being infected with HCV, comprising obtaining a preparation of cells from the individual, preparing exosome particles from the cellular supernatant and testing the exosome particles for the presence of HCV RNA and proteins. Preferably, the preparation of cells obtained from the individual is a blood plasma preparation.

Various aspects and embodiments of the present invention will now be described in more detail by way of example, with particular reference to the separation of exosomes using techniques of differential centrifugation and immunoseparation. It will be appreciated that modification of detail may be made without departing from the scope of the invention.

BRIEF DESCRIPTION OF THE FIGURES

FIG. 5 shows a Western blot demonstrating exosome capture from HCV-infected patients.

EXAMPLE 1

Preparation of Exosomes

Initially, exosomes were isolated from several cell lines, including hepatocellular carcinoma cell lines (HepG2 and HuH7) and EBV-transformed B cell lines. Cell cultures were first centrifuged for 10 min at 200×g and recovered cells represent pellet P1. Removed supernatant was centrifuged twice for 10 min at 500×g; the two pellets were pooled and represent pellet P2. Supernatants were sequentially centrifuged at 2000×g twice for 15 min (pooled pellets are referred to as P3), once at 10000×g for 30 min (recovered pellet represents pellet P4) and once at 70000×g for 60 min (yielding pellet P5).

Figure 1:
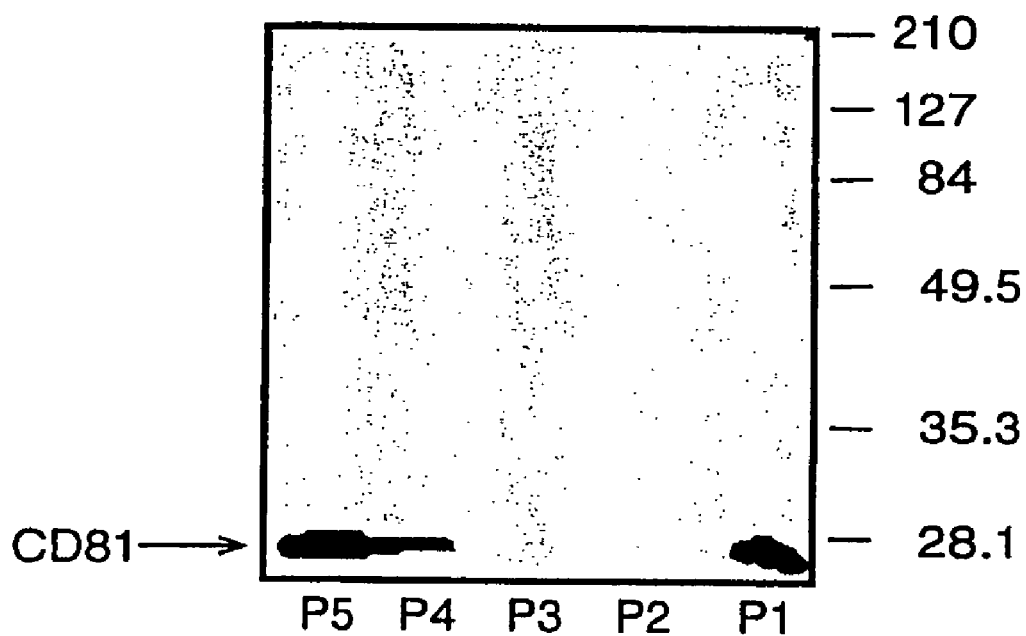
FIG. 1 shows a Western blot demonstrating exosome purification from HepG2 cell culture medium by differential centrifugation steps.

Samples of each pellet were then analysed in SDS-PAGE and Western blotting using anti-CD81 monoclonal antibody followed by peroxidase-labelled anti-mouse IgG. Pellet P5 was found to be the fraction enriched in exosomes (see FIG. 1). We have isolated exosomes from several cell lines, including hepatocellular carcinoma cell lines (HepG2 and HuH7) and EBV-transformed B cell lines.

Figure 2:
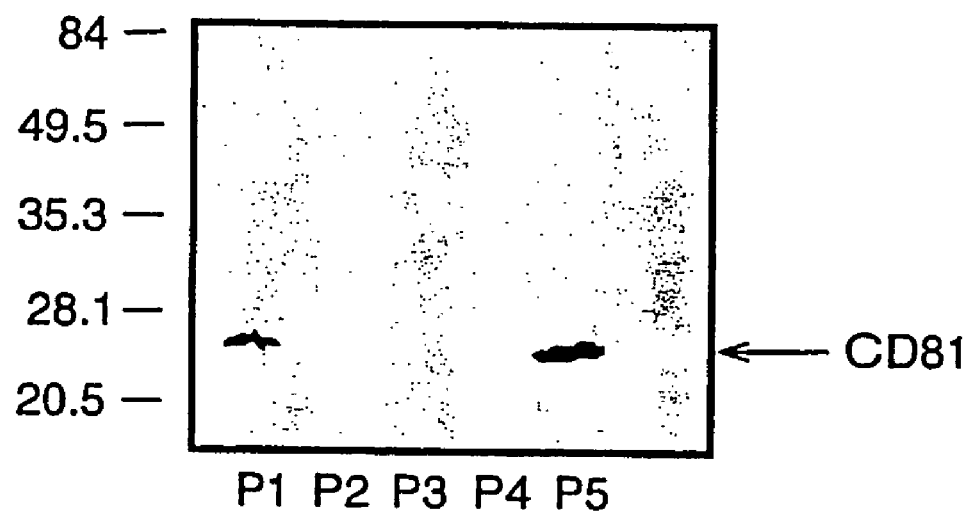
FIG. 2 shows a Western blot demonstrating exosome purification from human plasma by differential centrifugation steps.

Normal human plasma was subsequently assessed for the presence of exosomes. Diluted plasma recovered after blood separation on Ficoll gradients was processed according to the differential centrifugation protocol described above and exosomes were visualised by Western blot using anti-CD81 or anti-CD82 mAbs and peroxidase-labelled anti-mouse IgG. It has been found that there are exosomes in the plasma of healthy individuals (see FIG. 2).

Figure 3:
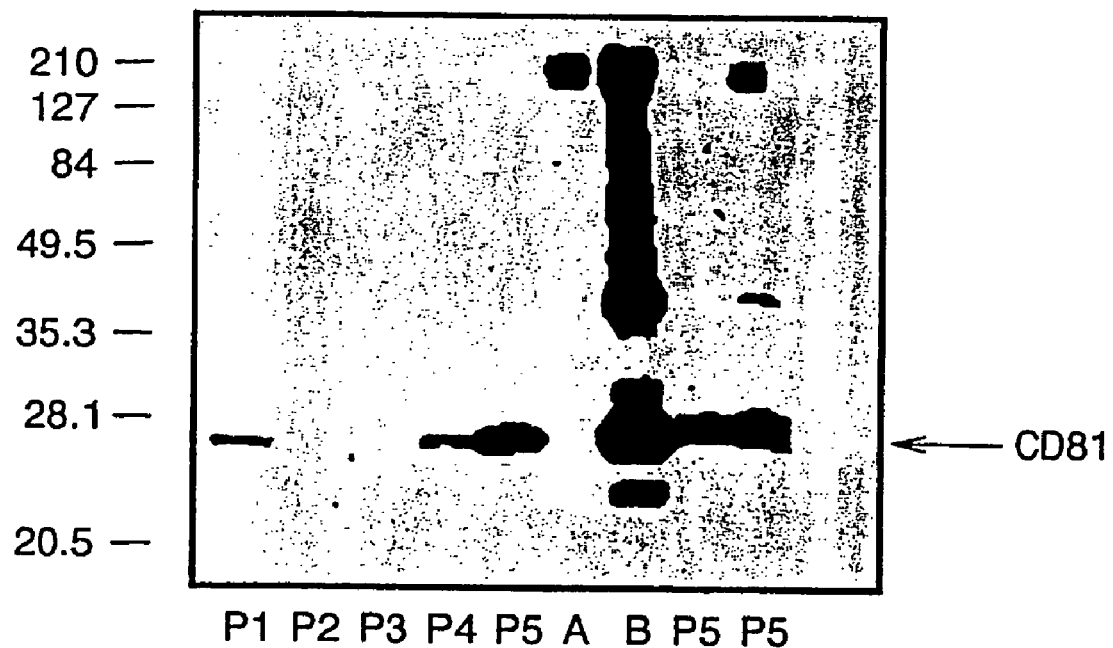
FIG. 3 shows a Western blot demonstrating exosome capture and sorting by anti-CD81-coated magnetic beads.
Figure 4:
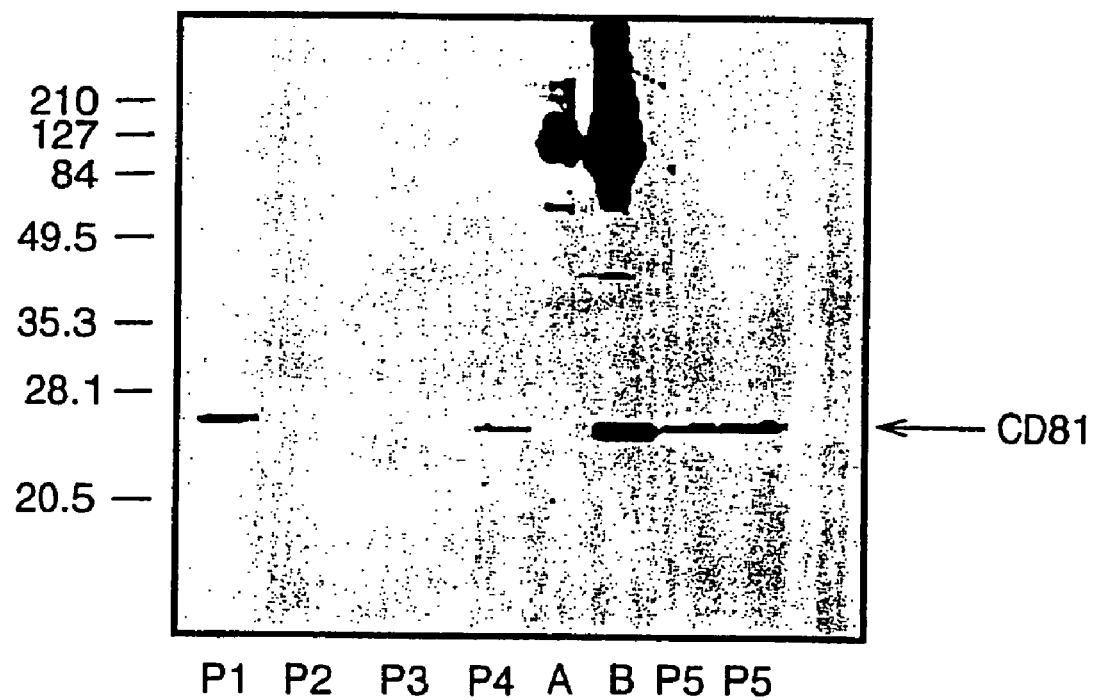
FIG. 4 shows a Western blot demonstrating exosome capture and sorting by anti-CD82-coated magnetic beads.

We have also succeeded in isolating exosomes from the supernatant before the centrifugation step at 70000×g by overnight incubation with magnetic beads previously coated with anti-CD81 or anti-CD82. Exosomes captured by anti-CD81-coated beads (see FIG. 3) or anti-CD82 coated beads (see FIG. 4) have been extracted twice with Laemmli buffer and detected by SDS-PAGE and Western blotting.

EXAMPLE 2

Preparation of HCV RNA

Given the results presented above, exosomes can now be isolated from plasma of HCV-infected patients enriched in HCV RNA. The experimental approach is as follows.

Plasma from HCV-infected human blood recovered after Ficoll separation is processed following the differential centrifugation protocol described above. The exosome-enriched supernatant collected from the centrifugation step at 10000×g is incubated overnight with anti-CD81-coated magnetic beads. Alternatively, after two clearing steps, HCV-infected plasma may be centrifuged at 20000×g before overnight incubation with anti-CD81-coated magnetic beads. Magnetic beads are then washed three times in 1% BSA in 50 mM Tris-HCl (pH 8.0), 1 mM EDTA, and 100 mM NaCl (TEN) buffer by magnetic separation and viral RNA are extracted with the Viral Extraction Kit (Qiagen). Quantitative RT-PCR for HCV RNA is performed as previously described (Pileri et al., 1998).

Alternative methods to capture exosomes from HCV-infected plasma may be tested, including the use of polystyrene beads (¼-inch diameter) as previously described (Pileri et al., 1998).

Exosomes in human plasma are enriched in HCV RNA and/or structural proteins.

EXAMPLE 3

Isolation of Exosomes from the Blood of HCV-Infected Patients

Here, we confirm the successful isolation of exosomes from the blood of HCV infected patients, either by steps of iterative centrifugation or by immunoselection with monoclonal antibodies against human CD81 or CD82 molecules, adopting the protocol used above for normal human plasma. Exosomes were then extracted in Laemmli buffer and CD81 (a marker enriched in exosomes) visualized by SDS-PAGE and Western blotting (see FIG. 5). This works confirms the presence of the CD81 protein in exosome preparations from the blood of an HCV patient.

Furthermore, in the exosomes prepared from infected patients, HCV RNA has been detected using quantitative RT PCR (see Table below).

Plasma from HCV-infected human blood recovered after Ficoll separation was processed following the differential centrifugation protocol described above. The exosome-enriched supernatant collected from the centrifugation step at 10000×g was incubated overnight with anti-CD81 or anti-CD82 coated magnetic beads (20 μg of purified monoclonal antibody/$2.5 \times 10^7$ magnetic beads (Dynal). Magnetic beads were then washed three times in 1% BSA in phosphate buffer by magnetic separation and viral RNA was extracted with the Trizol reagent (Life Technology).

Quantitative RT-PCR for HCV RNA was performed as previously described (Pileri et al., 1998).

TABLE

| \multicolumn{4}{c}{RT-PCR of HCV from exosomes derived from infected patients} | | | |
| Patient code | P4beads anti-CD81 | P4 beads alone | P5 |
| --- | --- | --- | --- |
| TORT | 1.25e4 | 5e3 | 3.2e5 |
| BREG | 6e2 | 1e2 | 6e4 |

REFERENCES

Escola J.-M. et al. (1998) J. Biol. Chem. 273: 20121-20127.
Harding C. V. and Geuze H. J. (1993) J. Immunol. 151: 3988-3998.
Neefjes J. J. et al. (1990) Cell 61: 171-183.
Pileri P. et al. (1998) Science 282: 938-941.
Raposo G. et al. (1996) J. Exp. Med. 183: 1161-1172.
Tulp A. et al. (1994) Nature 369: 120-126.

The invention claimed is:

1. A purified preparation of exosomes that comprise hepatitis C virus (HCV) RNA prepared by a method comprising separating exosome particles from the supernatant of a human cell culture infected with HCV using iterative centrifugation.

2. The preparation of claim 1, wherein the exosome particles are separated from the plasma of an individual infected with HCV.

3. The preparation of claim 1, wherein said exosome particles are enriched in CD81 protein.

4. A purified preparation of exosomes that comprise hepatitis C virus (HCV) RNA prepared by a method comprising separating exosome particles from the supernatant of a human cell culture infected with HCV, wherein said exosome particles are prepared from the cell culture supernatant by incubating the cell culture supernatant with beads coated with antibody.

5. The preparation of claim 4, wherein said antibody is anti-CD81 or anti-CD82 antibody.

6. The preparation of claim 4, wherein said beads are magnetic beads.

7. The preparation of claim 4, wherein said beads are polystyrene beads.

8. A preparation of exosomes that comprise hepatitis C virus (HCV) RNA prepared by a method comprising:
   (a) providing plasma from a subject infected with HCV;
   (b) subjecting the plasma to differential centrifugation to produce an exosome-enriched supernatant; and
   (c) incubating the supernatant with beads coated with an anti-CD81 or anti-CD82 antibody to isolate exosome particles.

9. The preparation of claim 8, wherein the subject is human.

10. The preparation of claim 8, wherein the supernatant is incubated with an anti-CD81 antibody.

11. The preparation of claim 10, wherein the supernatant is incubated with an anti-CD82 antibody.

12. The preparation of claim 8, wherein the beads are magnetic beads.

13. The preparation of claim 8, wherein the beads are polystyrene beads.

14. A preparation of exosomes that comprise hepatitis C virus (HCV) RNA prepared by a method comprising
  (a) providing plasma from a human infected with HCV;
  (b) subjecting the plasma to differential centrifugation to produce an exosome-enriched supernatant; and
  (c) incubating the supernatant with magnetic beads coated with an anti-CD81 or anti-CD82 antibody to isolate exosome particles.

* * * * *